(12) United States Patent
Manning et al.

(10) Patent No.: US 6,979,319 B2
(45) Date of Patent: Dec. 27, 2005

(54) TELESCOPING GUIDE CATHETER WITH PEEL-AWAY OUTER SHEATH

(75) Inventors: Frank E. Manning, Valley Center, CA (US); Charles R. Peterson, Murrieta, CA (US); Howard P. Graham, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 385 days.

(21) Appl. No.: 10/036,640

(22) Filed: Dec. 31, 2001

(65) Prior Publication Data

US 2003/0125619 A1 Jul. 3, 2003

(51) Int. Cl.$^7$ ............... A61M 31/00; A61M 5/178; A61M 5/00; A61B 18/18; A61N 1/00
(52) U.S. Cl. ............... 604/164.05; 604/95.04; 604/263; 606/41; 607/122
(58) Field of Search ............ 604/93.01, 95.01, 604/95.04, 158, 160, 161, 164.01, 164.05, 604/164.09, 164.1, 173, 263, 264, 523, 528, 604/533, 96.01, 101.04, 104, 915; 606/32, 606/41, 190–194; 607/1–5, 9, 17, 18, 28, 607/115, 116, 119, 122, 129; 600/372–374, 600/508, 509, 513, 515, 518, 101, 114–116

(56) References Cited

U.S. PATENT DOCUMENTS

| | | | |
|---|---|---|---|
| 4,432,752 A | 2/1984 | Marlon | |
| 4,586,923 A * | 5/1986 | Gould et al. | 604/95.04 |
| 4,596,559 A | 6/1986 | Fleischhacker | |
| 4,952,359 A * | 8/1990 | Wells | 264/139 |
| 5,120,299 A | 6/1992 | Lombardi | |
| 5,171,222 A | 12/1992 | Euteneuer et al. | |
| 5,190,528 A | 3/1993 | Fonger et al. | |
| 5,222,970 A | 6/1993 | Reeves | |
| 5,263,932 A | 11/1993 | Jang | |
| 5,320,602 A | 6/1994 | Karpiel | |
| 5,372,589 A | 12/1994 | Davis | |
| 5,454,790 A * | 10/1995 | Dubrul | 604/104 |
| 5,562,698 A | 10/1996 | Parker | |
| 5,765,682 A | 6/1998 | Bley et al. | |
| 5,775,327 A | 7/1998 | Randolph et al. | |
| 5,868,707 A | 2/1999 | Williams et al. | |
| 5,891,056 A | 4/1999 | Ramzipoor | |
| 5,964,730 A | 10/1999 | Williams et al. | |
| 6,002,956 A * | 12/1999 | Schaer | 600/381 |
| 6,022,342 A | 2/2000 | Mukherjee | |
| 6,090,135 A | 7/2000 | Plaia et al. | |
| RE36,857 E | 9/2000 | Euteneuer et al. | |
| 6,122,552 A | 9/2000 | Tockman et al. | |
| 6,277,107 B1 | 8/2001 | Lurie et al. | |
| 6,408,214 B1 * | 6/2002 | Williams et al. | 607/122 |
| 6,562,049 B1 * | 5/2003 | Norlander et al. | 606/108 |
| 6,659,959 B2 | 12/2003 | Brockway et al. | |
| 6,676,666 B2 | 1/2004 | Vrba et al. | |
| 6,755,812 B2 * | 6/2004 | Peterson et al. | 604/528 |

* cited by examiner

Primary Examiner—Nicholas D. Lucchesi
Assistant Examiner—Mark K. Han
(74) Attorney, Agent, or Firm—Hollingsworth & Funk, LLC

(57) ABSTRACT

A guide catheter employs a retractable inner guide movably disposed within an open lumen of a splittable outer guide. The outer guide includes a longitudinal pre-stress line extending from distal to proximal ends. The inner guide includes an open lumen adapted to receive a payload. The inner guide is translatable and rotatable relative to the outer guide. The guide catheter further includes a proximally attached guide handle which is separable into at least two sections. Separation of the guide handle splits the proximal end of the outer guide. Proximal outer guide retraction continues the splitting of the outer guide along the longitudinal pre-stress line.

25 Claims, 5 Drawing Sheets

TELESCOPING GUIDE CATHETER WITH PEEL-AWAY OUTER SHEATH

FIELD OF THE INVENTION

The invention relates generally to guide catheters, and more particularly to dual-sheath, telescoping guide catheters having a peel-away outer sheath used to locate and cannulate the coronary sinus of a patient's heart.

BACKGROUND OF THE INVENTION

Guiding catheters are instruments that allow a physician to locate and cannulate vessels in a patient's heart for preforming various medical procedures, including venography and implanting of cardiac pacing devices. Cannulating heart vessels requires navigating a small diameter, flexible guide through the convoluted vasculature into a heart chamber, and then into a destination heart vessel. Once the destination heart vessel is reached, the catheter acts as a conduit for insertion of payloads into the vessel.

A commonly accessed destination vessel for cardiac pacing lead insertion is the coronary sinus. A pre-shaped guiding catheter is typically used to blindly locate the coronary sinus ostium. This endeavor, however, is complicated by the fact that the location of the coronary sinus ostium may vary appreciably from one patient to another, especially among patients with diseased hearts. Oftentimes, the clinician is entirely unable to locate the coronary sinus ostium using the guiding catheter, and must resort to finding the ostium by "mapping" (interpreting localized bipolar waveforms) using an electrophysiological (EP) catheter and an ECG monitor. After the ostium is located, the guiding catheter is typically used to inject radiographic contrast media into the coronary sinus to highlight the associated venous system, and then a pacing lead is installed within one of the coronary branches.

Complicating this scenario is the dynamic structural deformation of the heart chambers that occurs from normal cardiac activity during the procedure. This further increases the difficulty of guiding a catheter to its destination. Presently, a considerable amount of time is often spent by the physician when manipulating such catheters within cardiac structures, such as the right atrium, simply trying to locate an anatomical feature of interest, such as the coronary sinus ostium.

Guiding catheter systems are typically configured with a profile that is optimized for the intended method of access. In the case of accessing the coronary sinus via the right atrium, a catheter with a distal contour including a relatively sharp bend will point the catheter towards the likely location of the coronary sinus once the right atrium is reached. The contours of pre-shaped guiding catheters are generally fixed, and this is typically achieved in production by constraining the distal end within a shaping fixture while warming them until they assume the intended shape (i.e., by "heat setting" their polymer shaft).

Guiding catheters are often designed to be relatively stiff at least along a substantial part of their proximal length. This allows easier insertion, as the stiffer catheter transmits pushing forces and is less likely to kink when encountering a bend or obstruction. However, a stiffer catheter is more prone to accidental dislodgment of payloads, such as pacing leads, when the catheter is retracted.

There is a need for an improved guide catheter that can dynamically account for anatomical variations and defects associated with the destination structures. There exists a further need for a guide catheter that provides for easier catheter insertion and yet is less likely to dislodge an implanted payload during catheter retraction. The present invention fulfills these and other needs, and addresses other deficiencies of prior art implementations and techniques.

SUMMARY OF THE INVENTION

The present invention is directed to a guide catheter for cannulating a vessel of a patient's heart. According to one embodiment of the invention, the guide catheter includes an outer guide having an open lumen and a longitudinal pre-stress line extending between a distal end and a proximal end of the outer guide. An inner guide having an open lumen is movably disposed within the open lumen of the outer guide such that the inner guide can rotate axially and translate longitudinally relative to the outer guide. The guide catheter further includes a guide handle. The guide handle has a distal end connected to the proximal end of the outer guide. The guide handle is separable into at least two sections such that guide handle separation splits the outer guide along the longitudinal pre-stress line at the proximal end of the outer guide. The outer guide further splits along the longitudinal pre-stress line upon outer guide retraction in a proximal direction relative to the inner guide.

In one aspect of the invention, the longitudinal pre-stress line on the outer guide includes a V-shaped notch on a surface of the outer guide. The outer guide can include a second longitudinal pre-stress line situated oppositely the first longitudinal pre-stress line on the surface of the outer guide. The second longitudinal pre-stress line may also include a V-shaped notch on a surface of the outer guide.

In one configuration, the guide catheter further includes a steering tendon disposed within the outer guide. A distal end of the steering tendon is connected to the distal end of the outer guide, such that the steering tendon deflects the distal end of the outer guide upon application of a tensile force to a proximal end of the steering tendon.

In another configuration, a steering mechanism is connected to the proximal end of the steering tendon. The steering mechanism applies a tensile force to the proximal end of the steering tendon. The steering mechanism can be connected to the guide handle. The steering mechanism may further include a steering handle pivotably mounted to the guide handle.

In one aspect of the invention, the distal end of the inner guide includes a pre-formed curve.

In another embodiment of the invention, the guide catheter further includes at least one electrode on the distal end of one or both of the inner guide and outer guide. At least one electrical conductor is coupled to the at least one electrode, the at least one conductor disposed within one or both of the inner guide and outer guide.

In another embodiment of the invention, an occlusion device may be connected near the distal end of the catheter. In one configuration, the occlusion device is connected to the distal end of the outer guide. In another configuration, the occlusion device is connected to the distal end of the inner guide.

In yet another embodiment of the invention, a guide catheter for delivery of a payload into a patient's heart includes an outer guide. The outer guide includes an open lumen and a longitudinal pre-stress line extending between a distal end and a proximal end of the outer guide. An inner guide is movably disposed within the open lumen of the outer guide such that the inner guide can rotate axially and translate longitudinally relative to the outer guide. The inner guide includes an open lumen adapted to receive the payload. The guide catheter further includes a guide handle. The guide handle has a distal end connected to the proximal end of the outer guide. The guide handle is separable into at least two sections such that guide handle separation splits the outer guide along the longitudinal pre-stress line at the proximal end of the outer guide. The outer guide further splits along the longitudinal pre-stress line upon outer guide retraction in a proximal direction relative to the inner guide. The inner guide secures the payload against dislodgment during outer guide retraction.

In another embodiment of the invention, a method of inserting a payload into a coronary sinus of a patient's heart includes providing a guide catheter having an outer guide, an inner guide, and a guide handle. The outer guide includes an open lumen and a longitudinal pre-stress line extending between the distal and proximal ends of the outer guide. The inner guide includes an open lumen adapted to receive the payload and is movably disposed within the open lumen of the outer guide. The inner guide can rotate axially and translate longitudinally relative to the outer guide. The guide handle includes a distal end connected to the proximal end of the outer guide. The guide handle is separable into at least two sections such that guide handle separation splits the outer guide along the longitudinal pre-stress line at the proximal end of the outer guide. The outer guide further splits along the longitudinal pre-stress line upon outer guide retraction in a proximal direction relative to the inner guide.

The method further involves inserting a distal end of the guide catheter through a patient's right atrium via an access vessel. The inner guide is axially extended and retracted relative to the outer guide to direct a distal end of the inner guide for finding and cannulating the patient's coronary sinus. A payload is inserted through the proximal end of the inner guide into the patient's coronary sinus.

The outer guide is removed by separating the guide handle into at least two sections to split the outer guide along the longitudinal pre-stress line. The outer guide is further split along the longitudinal pre-stress line by retracting the outer guide in a proximal direction relative to the inner guide. The inner guide secures the payload against dislodgment during outer guide retraction.

Another embodiment of the method involves distally advancing the outer guide over the inner guide to seat the outer guide in the coronary sinus after finding and cannulating the patient's coronary sinus. The inner guide is proximally retracted to remove the inner guide from the outer guide. The payload is then inserted through the proximal end of the outer guide to insert the payload into the patient's coronary sinus. The outer guide is removed by separating the guide handle into at least two sections to split the outer guide along the longitudinal pre-stress line. Then, retracting the outer guide in a proximal direction relative to the payload further splits the outer guide along the longitudinal pre-stress line.

In one aspect of the above methods, the payload includes a pacing lead. Another aspect of the methods involves the guide catheter further including a steering tendon disposed within the outer guide. A distal end of the steering tendon connects to the distal end of the outer guide. The steering tendon deflects the distal end of the outer guide upon application of a tensile force to a proximal end of the steering tendon. The methods further involve locating and cannulating the patient's coronary sinus by additionally applying a tensile force to the proximal end of the steering tendon to direct the distal end of the guide catheter.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
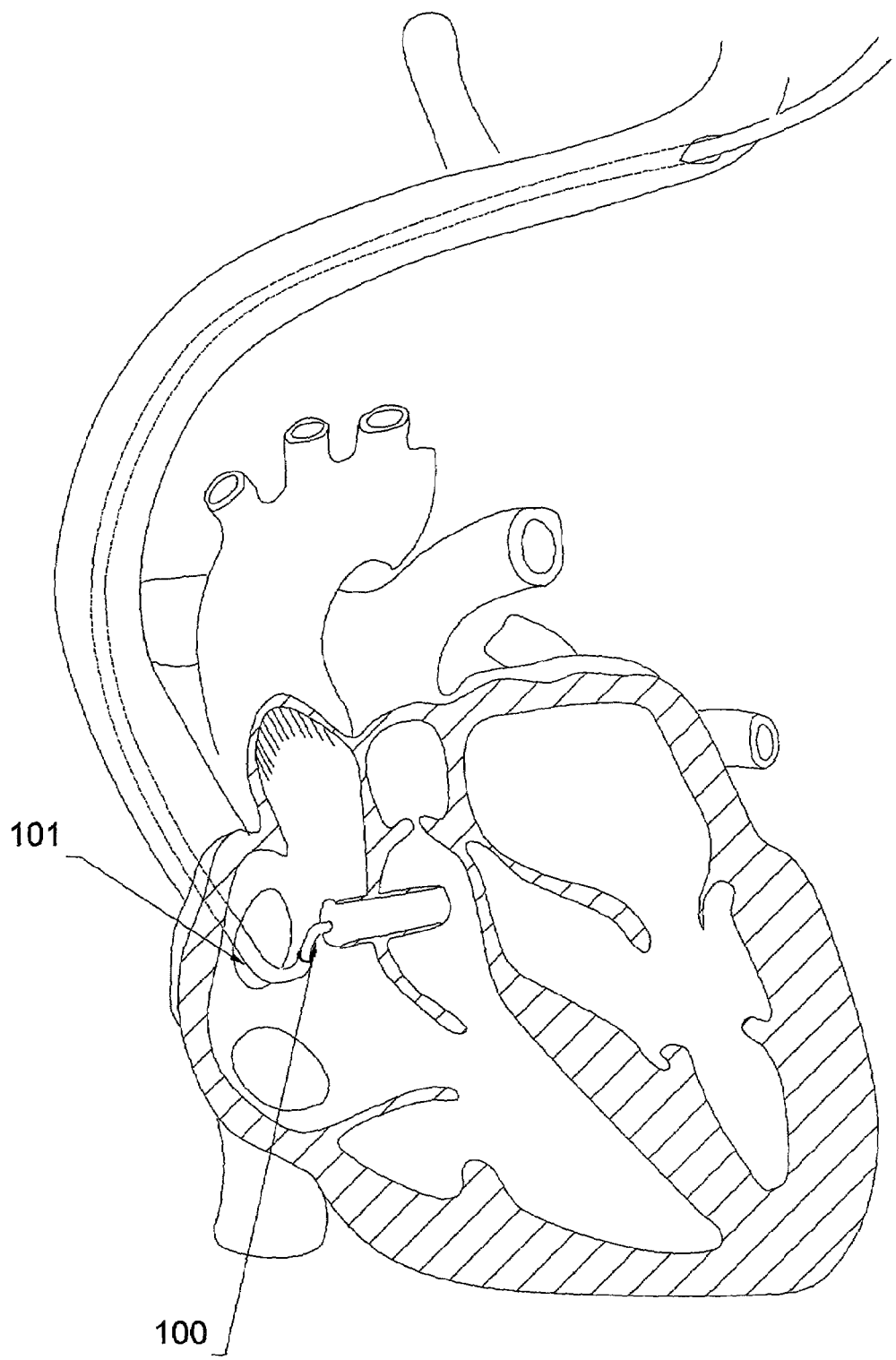
FIG. 1A is a cut-away view of a patient's heart, showing a catheter embodying features of the present invention deployed within the heart.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

With reference to FIG. 1A, a distal end of a guide catheter is illustrated in accordance with an embodiment of the present invention. The guide catheter includes an inner guide 100 and an outer guide 101. The guide catheter is shown deployed within a patient's heart, accessing the coronary sinus via the right atrium. A distal end of the inner guide 100 extends from the outer guide 101 as the inner guide 100 is advanced towards the coronary sinus ostium.

Figure 1B:
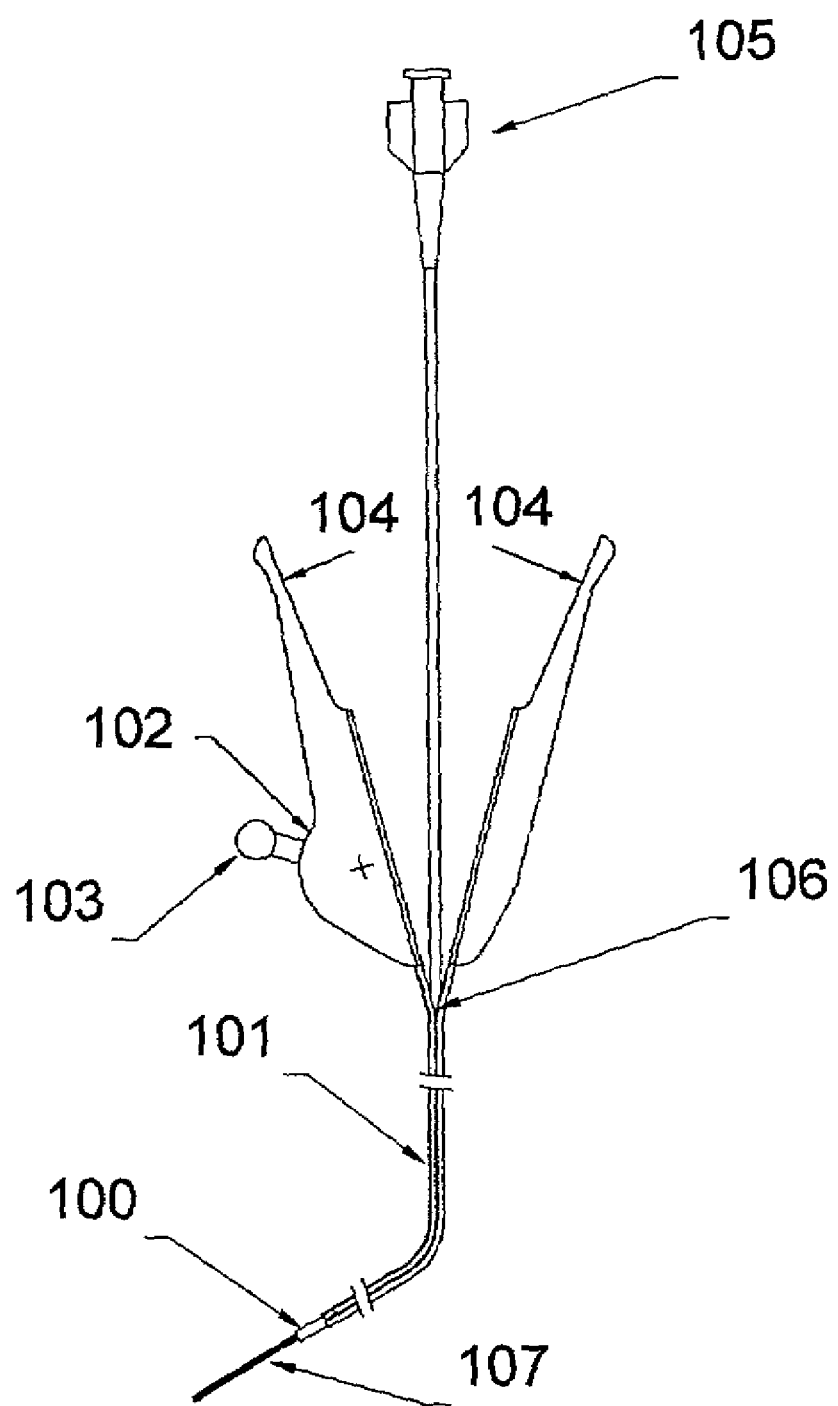
FIG. 1B is an external view of a catheter embodying features of the present invention.

Turning now to FIG. 1B, a guide catheter is shown embodying features of the present invention. The inner guide 100 is movably disposed within an open lumen of the outer guide 101 (best seen in FIG. 3B) such that the inner guide 100 can translate longitudinally and rotate axially within the outer guide 101. The inner guide 100 may contain a proximal attachment. In the embodiment shown in FIG. 1B, the proximal attachment is a wing luer 105. The inner guide 100 typically includes an open lumen (best seen in FIG. 3B), and the open lumen can be adapted to receive a payload 107.

The outer guide 101 is fixably attached to a distal end of a guide handle 102. The guide handle 102 includes a mechanism that facilitates separation of the guide handle 102 into at least two sections upon application of a splitting force 104. Separation of the guide handle 102 provides leverage to assist in easily splitting the outer guide 101. Once the outer guide 101 is split where the outer guide 101 attaches to the guide handle 102, proximal retraction of the outer guide 101 relative to the inner guide 100 can further split the outer guide 101.

The outer guide 101 is typically formed of a molded elastomer tubing. An elastomeric material such as a high durometer Pebax can provide the desired longitudinal stiffness. It is also possible to include an inner lubricious lining, formed from a material such as PTFE. The outer guide 101 may also include a soft distal tip to prevent tissue abrasion along the venous pathways.

The outer guide 101 includes a longitudinal pre-stress line 106 extending between the distal and proximal ends of the outer guide 101. The pre-stress line 106 is typically a V-shaped notch or groove formed on a surface of the outer guide 101. Other configurations of a pre-stress line are possible, such as a fiber or wire longitudinally embedded within the outer guide 101.

Figures 3A, 3B:
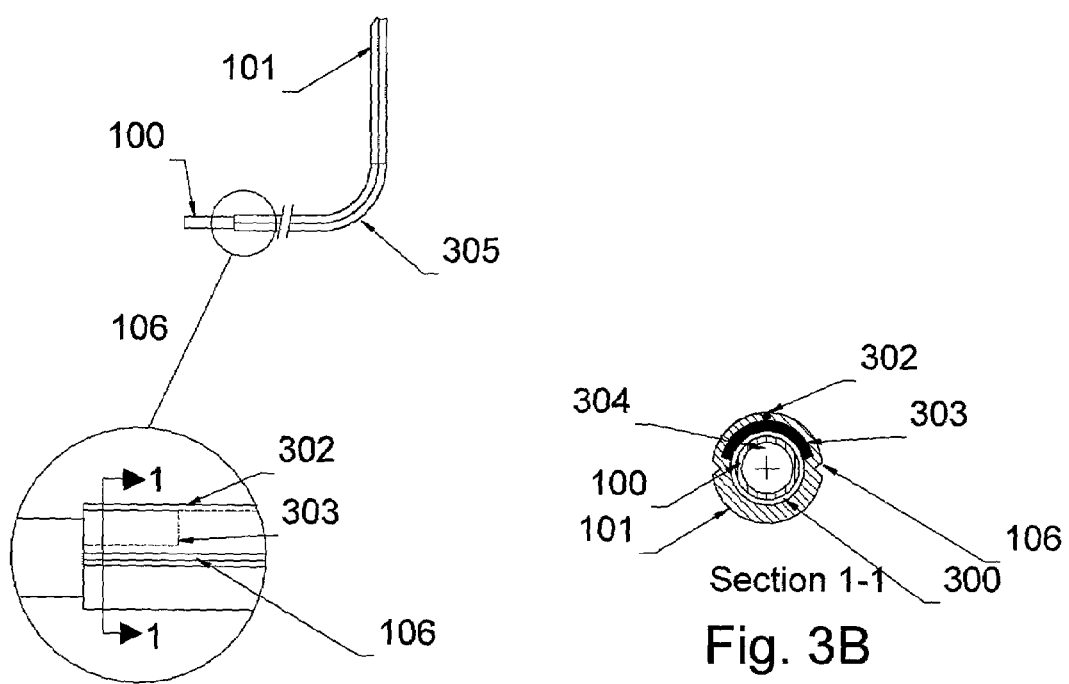
FIG. 3A is a view of the distal end of an outer guide of the present invention showing a steering tendon attachment.
FIG. 3B is a transverse cross section view of the distal end of the outer guide corresponding to Section 1—1 of FIG. 3A.

At least one pre-stress line 106 is required to allow splitting the outer guide 101. Two pre-stress lines 106 can be employed, the two pre-stress lines 106 typically being distributed oppositely (180 degrees apart) around a transverse cross sectional perimeter of the outer guide 101. The distribution of two pre-stress lines 106 on the outer guide 101 are best seen in FIG. 3B.

A guide catheter according to the present invention will generally be used to assist in implanting the payload 107 into a cardiac destination vessel. In one aspect of the present invention, the inner guide 100 is more compliant than the outer guide 101. A relatively rigid outer guide 101 is beneficial during insertion as it helps to prevent kinking and allows better transmittal of pushing forces. The inner guide 100 is commonly more flexible to afford greater maneuverability within a constricted heart chamber.

When a catheter embodying aspects of the present invention is advanced through the venous pathways, the inner guide 100 can be retracted within the outer guide 101. The inner guide 100 is relatively compliant compared to the outer guide 101, so the inner guide 100 tends to assume the shape of the outer guide 101 when retracted. Once the distal tip of the outer guide 101 has located a chamber of the heart, such as the right atrium, the flexible inner guide 100 is then extended from the distal end of the outer guide 101.

Figure 2A:
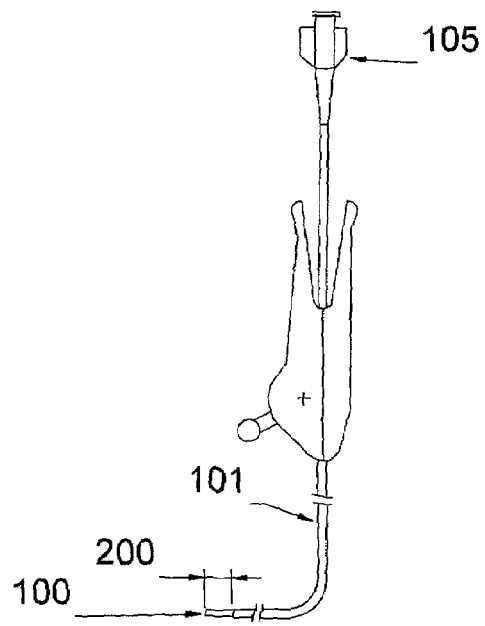
FIG. 2A is an external view of the catheter shown in FIG. 1B illustrating a retractable inner guide.
Figure 2B:
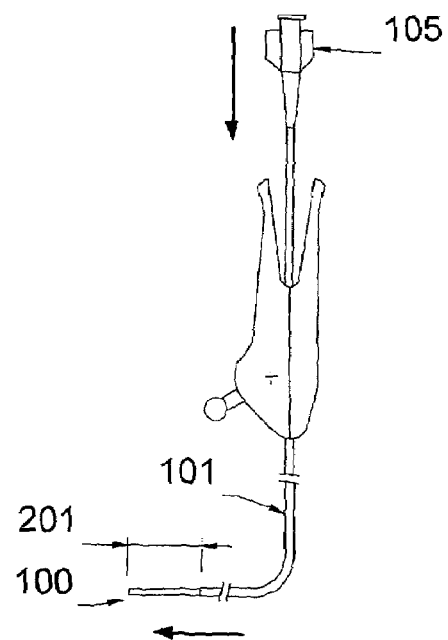
FIG. 2B is an external view of the catheter shown in FIG. 1B further illustrating the inner guide retraction.

FIGS. 2A and 2B illustrate extension of the inner guide 100 relative to the outer guide 101. In FIG. 2A, the distal end of the inner guide 100 extends from the outer guide 101 by a length 200. FIG. 2B show the result of pushing the proximal end of the inner guide 100, the direction of inner guide 100 movement being represented by the bold arrows. Pushing the inner guide 101 in the distal direction causes the extended length of the inner guide 100 to be increased to a length 201. The wing leuer 105 attached to the inner guide 100 can serve as a convenient grip from which to apply forces for adjustably extending and retracting the inner guide 100 while probing for the feature of interest at the distal end of the catheter.

Figure 4A:
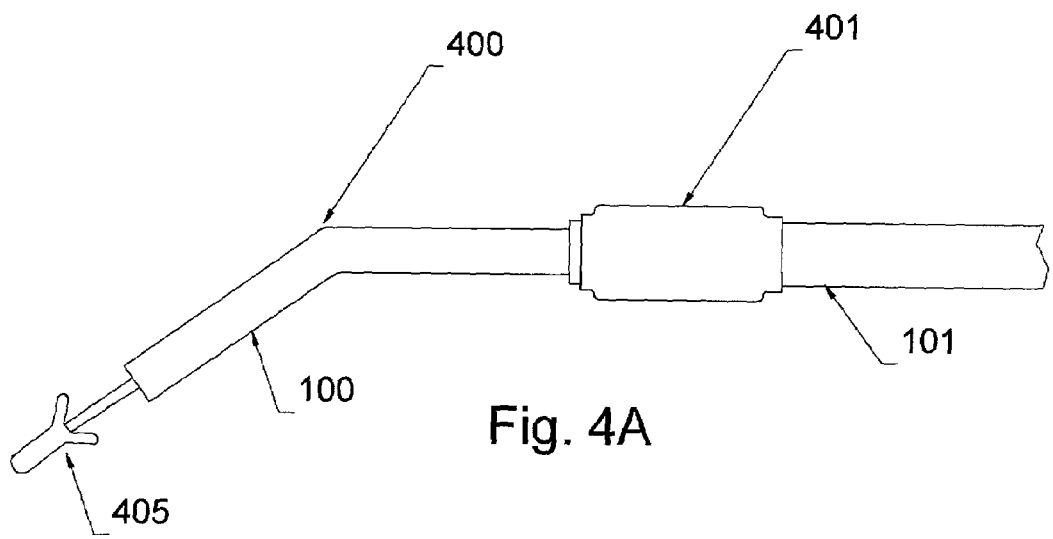
FIG. 4A is a view of the distal end of a catheter showing an occlusion balloon attached to the outer guide according to an embodiment of the present invention.

As is best seen in FIG. 4A, the inner guide 100 may also include a pre-formed curve 400. When the inner guide 100 is extended beyond the outer guide 101 within a heart chamber, the inner guide's distal end takes on the shape of the pre-formed curve 400. The pre-formed curve 400 can be optimized for locating a feature of interest. One common feature of interest in pacing lead implantation is the coronary sinus ostium, which is an access point to the coronary sinus. Pacing leads are often implanted in a destination vessel branching from the coronary sinus.

To allow optimal access to the coronary sinus ostium, the pre-formed curve 400 may include a bend angle ranging from about 20 to about 100 degrees. The pre-formed curve 400 may be located from about 1 centimeter to about 10 centimeters from the distal tip of the inner guide 100.

In one configuration, the inner guide 100 is formed from an extruded polymer tube with a thermoset pre-formed curve at the distal end. An elastomer such as Pebax may be used, usually in a lower durometer formulation that used in the outer guide 101. Typically, the inner guide 100 will have a lubricious lining along its inner surface. The inner guide 100 may include a soft distal tip to reduce tissue abrasion.

The extended distal end of the inner guide 100 can be rotated axially and extended longitudinally once it is in the access chamber of the heart. Extension and rotation of the inner guide 100 is useful in locating the feature of interest. Once the feature of interest is found, the inner guide 100 may be advanced as far as needed and seated within the destination vessel.

After the inner guide 100 is seated, a payload, such as a pacing lead 405, can be inserted through the inner guide 100. The pacing lead 405 is shown extending beyond the inner guide 100 in FIG. 4A. The pacing lead 405 is generally introduced into the inner guide 100 from the proximal end of the guide catheter. Once the pacing lead 405 is inserted into the destination vessel, the clinician may perform checks to determine if implantation was successful. For example, electrical measurements may be performed on the pacing lead 405 to ensure the pacing electrode has sufficiently contacted with the heart tissue to operate effectively.

After successful pacing lead 405 implantation, is necessary to remove the guide catheter from the venous pathway. The catheter may be designed to be relatively rigid to assist the insertion procedure, but this rigidity has a drawback during removal. When the catheter is being removed, a more rigid catheter will tend to displace the pacing lead 405.

The relatively compliant inner guide 100 with the splittable outer guide 101 according to the present invention can provide a guide catheter with advantages of both easy insertion and safe retraction. Referring again to FIG. 1B, retracting the catheter can begin by first splitting the outer guide 101. The guide handle 102 can be separated by applying a force 104 to appropriate locations of the handle. The guide handle 102 is fixably mounted to the outer guide's proximal end, so separation of the guide handle 102 also splits the proximal end of the outer guide 101.

Once the proximal end of the outer guide 101 is split, the outer guide 101 can be proximally retracted. Typically, the retraction is performed in such a manner as to impart a splitting force on the longitudinal pre-stress line 106 of the outer guide 101 as it is being pulled out of the entry point.

In a case where the outer guide 101 includes two longitudinal pre-stress lines 106, outer guide splitting can be accomplished by grasping each split half of the outer guide 101 and pulling at an angle that provides both axial and radial forces, thus retracting and splitting the outer guide 101 at the same time.

The splitting of the outer guide 101 is beneficial as it allows the outer guide 101 to be removed without the guide 101 disturbing any attachments that may be mounted on the proximal end of inner guide 100. For example, a wing luer 105 may be mounted to the proximal end of the inner guide 100, as shown in FIG. 1B. Splitting the outer guide 101 during outer guide retraction enables the outer guide 101 to be retracted without interfering with the wing luer 105. Splitting the outer guide 101 also enables the clinician to secure the inner guide 100 near the percutaneous access point during outer guide 101 retraction.

While the outer guide 101 is being retracted, the inner guide 100 helps to prevent dislodgment of the payload 107. The outer guide 101 will typically impart axial shear forces on the inner guide 100 during outer guide 101 retraction. The inner guide 100 can be held secure by the clinician to resist the axial shear forces. The inner guide 100 is typically better able to resist being dislodged during outer guide 101 retraction than is the payload 107. If the inner guide 100 is dislodged, a lubricious lining within the inner guide 100 helps ensure that only minimal disruptive forces act on the payload 107. The inner guide 100, if dislodged, can be re-seated as necessary during the outer guide 101 retraction procedure.

After the outer guide 101 has been fully removed, the inner guide 100 will still effectively cannulate a path to the destination vessel until such time as inner guide 100 removal is required. The inner guide 100 is relatively compliant and may have an inner lubricious lining, so retraction of the inner guide 100 is less likely to dislodge the payload 106.

In an alternate method, it may be desirable to utilize the outer guide 101 to cannulate the destination vessel. The outer guide 101 has a larger lumen than the inner guide 100, and can accommodate a larger payload. In this method, the destination vessel is located and cannulated by the inner guide 100 as previously described. The outer guide 101 is then distally advanced over the inner guide 100 until the outer guide 101 is seated in the destination vessel. The inner guide 100 can then be proximally retracted until it is removed from the outer guide 101.

In this alternate method, the payload 106 can then be advanced through the lumen of the outer guide 101. When the procedure requires removal of the guide catheter, the outer guide 101 can be split at the guide handle 102 as previously described. The outer guide 101 is further split while being proximally retracted. The splitting serves to prevent interference between the outer guide 101 and any proximal attachments that may be connected to the payload 106.

Turning now to FIG. 3A, another embodiment of the present invention is shown that includes a steering tendon 302 and a deflection location 305. The steering tendon 302 and deflection location 305 are used to assist guiding the distal end of the guide catheter during insertion.

The steering tendon 302 typically attaches to the distal end of the outer guide 101. The steering tendon 302 allows the distal end of the outer guide 101 to be deflected and thereby assists the inner guide 100 in locating the feature of interest. FIG. 3B illustrates a configuration at the outer guide distal end where the steering tendon 320 is attached to a steering plate 303. The steering plate 303 is semi-circular in shape and is fixedly attached to the distal end of the outer guide 101.

The steering tendon 302 can be accessed from the proximal end of the guide catheter. Application of a pulling force on the steering tendon 302 causes the outer guide 101 to deflect at the deflection location 305. In one configuration, the guide catheter can include a steering handle 103 that can provide convenient control of the steering tendon 302. The steering handle 103 is typically pivotably attached to the guide handle 101. The steering handle 103 connects to the steering tendon 302 and applies a tensile force on the steering tendon 302.

It may be useful to orient the steering tendon 302 and the deflection location 305 perpendicular to the longitudinal pre-stress line 106. As shown in FIG. 3B, two longitudinal pre-stress lines 106 are both 90 degrees from the steering tendon 302 when viewed from a transverse cross section.

The deflection location 305 is typically preformed in the outer guide 101 during manufacture. A number of fabrication methods for forming the deflection location 305 are possible, and such methods are well known in the art. One such method is to mold or thermoset a bend in the outer guide 101. Another method for forming a deflection location 305 is to impart a change in stiffness in the outer guide 101 at the desired location. A change in stiffness can be created by altering outer guide 101 wall geometry (e.g. diameter, wall thickness) or by making a transition in wall materials at the region of the deflection location 304.

Figure 2C:
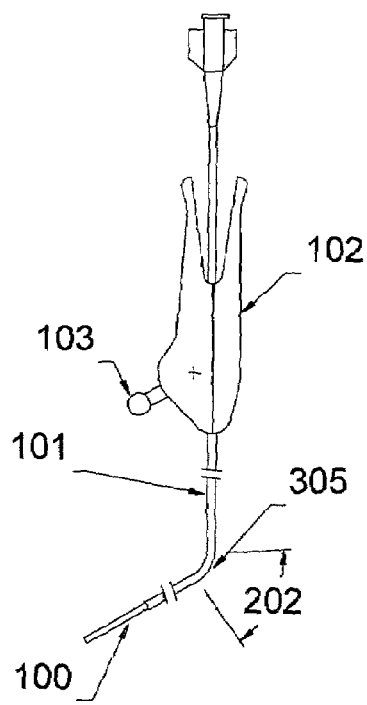
FIG. 2C is an external view of the catheter shown in FIG. 1B illustrating a deflectable outer guide.
Figure 2D:
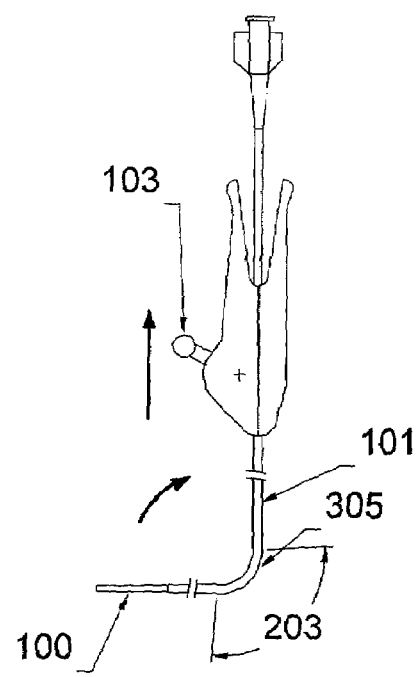
FIG. 2D is an external view of the catheter shown in FIG. 1B further illustrating the outer guide deflection.

FIGS. 2C and 2D illustrate the action of the steering tendon 302 on the outer guide 101. In FIG. 2C, the outer guide has an initial bend angle 202 at a deflection location 305. FIG. 2D shows the effect of applying a force on the handle 103, the direction of movement being represented by the bold arrows. Pulling the handle 103 in a proximal direction applies a tensile force to the steering tendon 302. The tensile force on the steering tendon 302 in turn causes the deflection location 305 of the outer guide 101 to assume a new angle 203. The angle 203 can be adjusted to assist in directing the distal end of the inner guide 100 to the feature of interest. The initial angle 202 may range from about 0 to about 100 degrees. The steering tendon 302 can impart a change of up to about 45 degrees on the initial angle 202, depending on catheter geometry.

Turning now to FIG. 4A, another embodiment of the catheter according to the present invention is illustrated. FIG. 4A illustrates a pre-formed bend 400 on the inner guide 100. A pacing lead 405 is shown extending from the distal end of the inner guide 100. The pacing lead 405 is a typical payload for a guide catheter embodying features of the present invention.

The guide catheter illustrated in FIG. 4A also employs an occlusion balloon 401 on the distal tip of the outer guide 101. The occlusion balloon 401 can be inflated when the outer guide 101 is in a vessel where blood flow occlusion is desired. Blood flow can be temporarily occluded in this way before injecting a contrast media, for example. The occlusion balloon 401 is typically inflated by a fluid injected from a proximal end of the outer guide 101. Methods of mounting and actuating the occlusion balloon 401 are well known in the art.

Figure 4B:
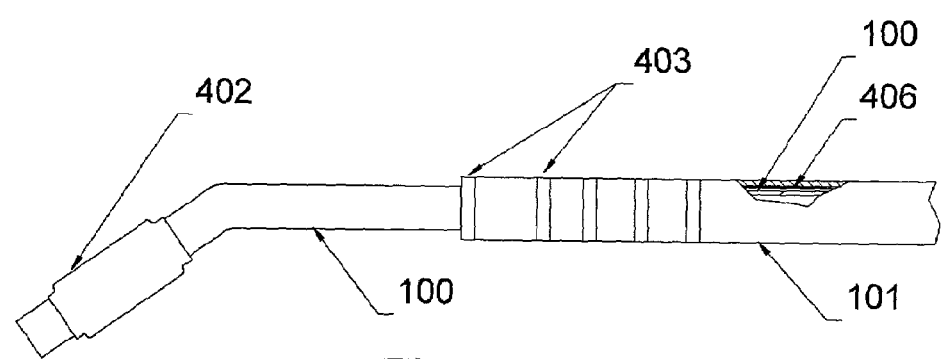
FIG. 4B is a view of the distal end of a catheter showing electrodes provided at the distal end of the outer guide and an occlusion balloon provided at the distal end of the inner guide according to another embodiment of the present invention.

FIG. 4B illustrates an occlusion balloon 402 mounted on the distal end of the inner guide 100. Actuation and disposition of the occlusion balloon 402 is similar to that described for the occlusion balloon 401 mounted on the outer guide 101. In another aspect of the invention, the payload 107 (as seen in FIG. 1B) may include an occlusion device.

Figure 4C:
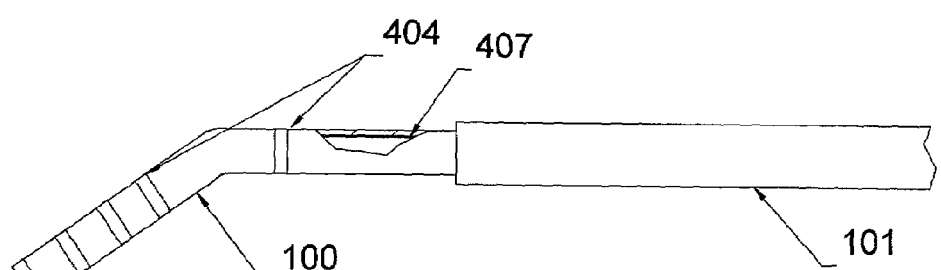
FIG. 4C is a view of the distal end of a catheter showing electrodes provided at the distal end of the inner guide according to a further embodiment of the present invention.

Also shown in FIG. 4B are electrodes 403 mounted on the distal end of the outer guide 101. The electrodes 403 are typically flush mounted, and are connected to at least one conductor 406 that is disposed between the distal and proximal ends of the inner guide 100. FIG. 4C shows electrodes 404 mounted in a similar fashion, but in this case mounted on the inner guide 100. The electrodes 404 are connected to at least one conductor 407 that is disposed between the distal and proximal ends of the inner guide 100. The electrodes 403 and 402 can be used for electrophysiological (EP) purposes, such as EP mapping structures within the heart. Those skilled in the art will appreciate that other measurement devices, such as a piezoelectric crystal for measuring fluid pressure, can also be mounted on the inner and outer guides 100, 101 in a similar fashion as described for the electrodes 402, 403.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A guide catheter having proximal and distal ends, comprising:
    an outer guide having an open lumen and a longitudinal pre-stress line extending between a distal end and a proximal end of the outer guide;
    an inner guide having an open lumen, the inner guide movably disposed within the open lumen of the outer guide such that the inner guide can rotate axially and translate longitudinally relative to the outer guide;
    a guide handle having a distal end connected to the proximal end of the outer guide, the guide handle separable into at least two sections such that guide handle separation splits the outer guide along the longitudinal pre-stress line at the proximal end of the outer guide, the outer guide further splitting along the longitudinal pre-stress line upon outer guide retraction in a proximal direction relative to the inner guide; and
    a steering member disposed along the outer guide, a distal end of the steering member connected at a distal end of the outer guide, and a proximal end of the steering member accessible at the proximal end of the outer guide, whereby application of a tensile force to the proximal end of the steering member effects deflection of the distal end of the outer guide.

2. A guide catheter according to claim 1, wherein the longitudinal pre-stress line comprises a V-shaped notch on a surface of the outer guide.

3. A guide catheter according to claim 2, wherein the outer guide further comprises a second longitudinal pre-stress line situated opposite the longitudinal pre-stress line on the surface of the outer guide.

4. A guide catheter according to claim 3, wherein the second longitudinal pre-stress line comprises a V-shaped notch on a surface of the outer guide.

5. A guide catheter according to claim 1, wherein the steering member comprises a steering tendon disposed within the outer guide, a distal end of the steering tendon connected to the distal end of the outer guide, such that the steering tendon deflects the distal end of the outer guide upon application of a tensile force to a proximal end of the steering tendon.

6. A guide catheter according to claim 5, further comprising a steering mechanism connected to the proximal end of the steering tendon, the steering mechanism applying a tensile force to the proximal end of the steering tendon.

7. A guide catheter according to claim 6, wherein the steering mechanism is connected to the guide handle.

8. A guide catheter according to claim 7, wherein the steering mechanism includes a steering handle pivotably mounted to the guide handle.

9. A guide catheter according to claim 1, wherein a distal end of the inner guide includes a pre-formed curve.

10. A guide catheter according to claim 1, further comprising:
    at least one electrode on the distal end of one or both of the inner guide and outer guide; and
    at least one electrical conductor coupled to the at least one electrode, the at least one conductor disposed within one or both of the inner guide and outer guide.

11. A guide catheter according to claim 1, further comprising an occlusion device connected to the distal end of the outer guide.

12. A guide catheter according to claim 1, further comprising an occlusion device connected to a distal end of the inner guide.

13. A guide catheter for delivery of a payload into a patient's heart, comprising:
    an outer guide having an open lumen and a longitudinal pre-stress line extending between a distal end and a proximal end of the outer guide;
    an inner guide having an open lumen adapted to receive the payload, the inner guide movably disposed within the open lumen of the outer guide such that the inner guide can rotate axially and translate longitudinally relative to the outer guide, the inner guide having a stiffness less than that of the outer guide;
    a guide handle having a distal end connected to the proximal end of the outer guide, the guide handle separable into at least two sections such that guide handle separation splits the outer guide along the longitudinal pre-stress line at the proximal end of the outer guide, the outer guide further splitting along the longitudinal pre-stress line upon outer guide retraction in a proximal direction relative to the inner guide, the stiffness of the inner guide relative to the outer guide sufficient to inhibit dislodgment of the payload as the outer guide moves in a proximal direction over the inner guide during outer guide retraction; and
    a steering member disposed along the outer guide, a distal end of the steering member connected at a distal end of the outer guide, and a proximal end of the steering member accessible at the proximal end of the outer guide, whereby application of a tensile force to the proximal end of the steering member effects deflection of the distal end of the outer guide.

14. A guide catheter according to claim 13, wherein the longitudinal pre-stress line comprises a V-shaped notch on a surface of the outer guide.

15. A guide catheter according to claim 14, wherein the outer guide further comprises a second longitudinal pre-stress line situated opposite the longitudinal pre-stress line on the surface of the outer guide.

16. A guide catheter according to claim 15, wherein the second longitudinal pre-stress line comprises a V-shaped notch on a surface of the outer guide.

17. A guide catheter according to claim 13, wherein the steering member comprises a steering tendon disposed within the outer guide, a distal end of the steering tendon connected to the distal end of the outer guide, such that the steering tendon deflects the distal end of the outer guide upon application of a tensile force to a proximal end of the steering tendon.

18. A guide catheter according to claim 13, further comprising a steering mechanism connected to the proximal end of the steering member, the steering mechanism applying the tensile force to the proximal end of the steering member.

19. A guide catheter according to claim 18, wherein the steering mechanism is connected to the guide handle.

20. A guide catheter according to claim 18, wherein the steering mechanism comprises a steering handle pivotably mounted to the guide handle.

21. A guide catheter according to claim 13, wherein a distal end of the inner guide includes a pre-formed curve.

22. A guide catheter according to claim 13, further comprising:
- at least one electrode on the distal end of one or both of the inner guide and outer guide; and
- at least one electrical conductor coupled to the at least one electrode, the at least one conductor disposed within the one or both of the inner guide and outer guide.

23. A guide catheter according to claim 13, further comprising an occlusion device connected to the distal end of the outer guide.

24. A guide catheter according to claim 13, further comprising an occlusion device connected to a distal end of the inner guide.

25. A guide catheter according to claim 13, wherein the payload comprises a pacing lead.

* * * * *

UNITED STATES PATENT AND TRADEMARK OFFICE
CERTIFICATE OF CORRECTION

PATENT NO. : 6,979,319 B2  Page 1 of 1
DATED : December 27, 2005
INVENTOR(S) : Manning et al.

It is certified that error appears in the above-identified patent and that said Letters Patent is hereby corrected as shown below:

Column 1,
Line 15, "preforming various" should read -- performing various --.

Column 5,
Line 64, "show the result" should read -- shows the result --.
Line 67, "inner guide 101" should read -- inner guide 100 --.

Column 6,
Line 2, "wing leuer 105" should read -- wing luer 105 --.
Line 25, "that used in" should read -- that is used in --.
Line 27, "implantation, is" should read -- implantation, it is --.

Column 7,
Line 10, "end of inner" should read -- end of the inner --.
Line 37, "the payload 106." should read -- the payload 107. --.
Line 48, "the payload 106" should read -- the payload 107 --.
Line 56, "106." should read -- 107 --.
Line 67, "tendon 320 is" should read -- tendon 302 is --.

Column 8,
Line 12, "handle 101." should read -- handle 102. --.

Column 9,
Line 14, "electrodes 403 and 402" should read -- electrodes 403 and 404 --.
Line 20, "electrodes 402, 403." should read -- electrodes 403, 404. --.

Signed and Sealed this

Fourth Day of April, 2006

JON W. DUDAS
*Director of the United States Patent and Trademark Office*